United States Patent
Wang et al.

(10) Patent No.: US 7,851,230 B2
(45) Date of Patent: Dec. 14, 2010

(54) STRESS-INDUCED PHOSPHOPROTEIN 1 AS A BIOMARKER FOR THE DETECTION OF HUMAN OVARIAN CANCERS AND ENDOMETRIOSIS

(75) Inventors: Tzu-Hao Wang, Taoyuan County (TW); Shun-Hua Chen, Taoyuan County (TW)

(73) Assignee: Chang Gung Memorial Hospital, Taipei (TW)

( * ) Notice: Subject to any disclaimer, the term of this patent is extended or adjusted under 35 U.S.C. 154(b) by 116 days.

(21) Appl. No.: 12/102,807

(22) Filed: Apr. 14, 2008

(65) Prior Publication Data

US 2009/0258378 A1   Oct. 15, 2009

(51) Int. Cl.
G01N 33/536 (2006.01)
(52) U.S. Cl. .................. 436/536; 435/6; 435/7.23; 436/518
(58) Field of Classification Search ............. None
See application file for complete search history.

(56) References Cited

U.S. PATENT DOCUMENTS

| | | | |
|---|---|---|---|
| 7,189,507 | B2 | 3/2007 | Mack et al. |
| 7,655,471 | B2 * | 2/2010 | Byrjalsen et al. ........ 436/64 |
| 2004/0096915 | A1 | 5/2004 | Diamandis | |

FOREIGN PATENT DOCUMENTS

WO    WO 99/57565    11/1999

OTHER PUBLICATIONS

Jean-Philippe Gagné et al., Jul. 2005, Molecular and Cellular Biochemistry, vol. 275, pp. 25-55.*
Van Calster, B., et al, *Discrimination Between Benign and Malignant Adnexal Masses by Specialist Ultrasound Examination Versus Serum CA-125*, J. Nat. Cancer Inst., vol. 99, Issue 22, Nov. 21, 2007, pp. 1706-1714.
Robertson, D.M., et al, *Inhibin as a diagnostic marker for ovarian cancer*, ScienceDirect, Cancer Letters, (2007), vol. 249, pp. 14-17.
Hanash, S., *Disease protomics*, Nature, Mar. 13, 2003, vol. 422, pp. 226-232.
Hanash, S., *HUPO Initiatives Relevant to Clinical Proteomics*, Molecular & Cellular Proteomics 3.4, (2004), pp. 298-301.
Cells, J.E., et al, *Proteomic Characterization of the Interstitial Fluid Perfusing the Breast Tumor Microenvironment*, Molecular & Cellular Proteomics 3.4, (2004), pp. 327-344.
Cells, J.E., et al., *Towards discovery-driven translational research in breast cancer*, FEBS Journal, (2005), vol. 272, pp. 2-15.
Wang, T., et al, *Microtubule-interfering Agents Activate e-Jun N-terminal Kinase/Stress activated Proein Kinase through Both Ras and Apoptosis Signal-regulating Kinase Pathways*, The Journal of Biological Chemistry, Feb. 27, 1998, vol. 273, No. 9, pp. 4928-4936.

Wang, T., et al., *Microtubule Dysfunction Induced by Paclitazel Initiates Apoptosis through Both c-Jun N-terminal Kinase (JNK)-dependent and -Independent Pathways in Ovarian Cancer Cells*, The Journal of Biological Chemistry, Mar. 19, 1999, vol. 274, No. 12, pp. 8208-8216.
Hsieh, S., et al., *Comparative proteomic studies on the pathogenesis of human ulcerative colitis*, Proteomlcs, (2006), vol. 6, pp. 5322-5331.
Wang, T., et al, *Paclitazel (Taxol) upregulates expression of functional interleukin-6 inhuman ovarian cancer cells through multiple signaling pathways*, Oncogene, (2006), vol. 25, pp. 4857-4866.
Wang, T., et al, *Insulin-like growth factor-II (IGF-II), IGF-binding protein-3 (IGFBP-3), and IGFBP-4 in follicular fluid are associated with oocyte maturation and embryo development*, Fertility and Sterility, Nov. 5, 2006, vol. 86, No. 5, pp. 1392-1401.
Chao, A., et al., *Molecular characterization of adenocarcinoma and squamous carcinoma of the uterine cervix using microarray analysis of gene expression*, Int. J. Cancer, (2006), vol. 119, pp. 91-98.
Zweig, M.H., *ROC Plots Display Test Accuracy, but Are Still Limited by the Study Design*, Clinical Chemistry, (1993), vol. 39, No. 6, pp. 1345-1346.
Americano, T.A., et al., *Signaling induced by hop/STI-1 depends on endocytosis*, Biochem. Biophys. Research Comm., (2007), vol. 358, pp. 20-625.
Yi, X., et al., *Association of Mortalin (HSPA9) with Liver Cancer Metastasis and Prediction for Early Tumor Recurrence*, Molecular & Cellular Proteomics 7.2, (2008), pp. 315-325.
Odunuga, O.O. et al, *Hop: more than an Hsp70/Hsp90 adaptor protein*, Bioessays, (2004), vol. 26, pp. 1058-1068.
Longshaw, V.M., et al., *Nuclear translocation of the Hsp70/Hsp90 organizing protein mSTI1 is regulated by cell cycle kinases*, Journal of Cell Science, (2004), vol. 117, pp. 701-710.
Sun, W., et al., *Proteome Analysis of Hepatocellular Carcinoma by Two-dimensional Difference Gel Electrophoresis*, Molecular & Cellular Proteomics, 6.10, (2007), pp. 1798-1808.
Erlich, R.B., et al., *STI1 Promotes Glioma Proliferation Through MAPK and PI3K Pathways*, GLIA, (2007), vol. 55, pp. 1690-1698.
Yin, B.W.T., et al., *Molecular Cloning of the CA125 Ovarian Cancer Antigen*, Journal of Biological Chemistry, Jul. 20, 2001, vol. 276, No. 29, pp. 27371-27375.
Yin, B.W.T., et al., *Ovarian Cancer Antigen CA125 is encoded by the MUC16 Mucin Gene*, Int. J. Cancer, (2002), vol. 98, pp. 737-740.
Rump, A., et al., *Binding of Ovarian Cancer Antigen CA125/MUC16 to Mesothelin Mediates Cell Adhesion*, The Journal of Biological Chemistry, Mar. 5, 2004, vol. 279, No. 10, pp. 9190-9198.
Gubbels, Jennifer AA, et al., *Mesothelin-MUC16 binding is a high affinity, N-glycan dependent interation that facilitates peritoneal metastasis of ovarian tumors*, Molecular Cancer, (2006), vol. 5 No. 50, pp. 1-15.
Bredemeyer, A.J., et al., *Hop Cleavage and Function in Granzyme B-induced Apoptosis*, The Journal of Biological Chemistry, (2006), vol. 281, No. 48, pp. 37130-37141.

* cited by examiner

*Primary Examiner*—Misook Yu
(74) *Attorney, Agent, or Firm*—Christie, Parker & Hale, LLP (57) ABSTRACT

Disclosed herein is a method for the detection, preliminary screening or monitoring of a gynecological disease selected form ovarian cancers and endometriosis, in which STIP1 is used as a biomarker for the gynecological disease.

15 Claims, 8 Drawing Sheets

STRESS-INDUCED PHOSPHOPROTEIN 1 AS A BIOMARKER FOR THE DETECTION OF HUMAN OVARIAN CANCERS AND ENDOMETRIOSIS

BACKGROUND OF THE INVENTION

1. Field of the Invention

This invention relates to the finding of stress-induced phosphoprotein 1 (STIP1) as a biomarker for the detection of human ovarian cancers and endometriosis. Based on said finding, this invention provides a method for the detection, preliminary screening or monitoring of a gynecological disease selected form ovarian cancers and endometriosis, in which STIP1 is used as a biomarker for the gynecological disease.

2. Description of the Related Art

Ovarian cancer is the leading cause of gynecological cancer death. The high case-fatality rate of ovarian cancer is mainly attributed to the fact that most ovarian cancers are diagnosed in advanced stages, III or IV, where the cancer has spread beyond the pelvis. On the contrary, stage I ovarian cancer that is limited to the ovaries has a survival rate of over 90 percent. Early detection of ovarian cancer appears to be the best strategy for reducing ovarian cancer mortality.

The majority (90%) of ovarian cancer is epithelial origin, including the serous type (70%), mucinous (10%), and endometrioid (10%). The remaining 10% originates from germ cell or stromal sex cord. Measurement of serum levels of a glycoprotein, CA125, has become standard practice for the preoperative evaluation of ovarian masses (Ben Van Calster et al. (2007), *J. Natl. Cancer Inst.,* 99(22):1706-1714). However, the overall sensitivity of detecting ovarian cancer is about 80%, with the highest in serous type (94%) and the lowest in granulose cell tumor (30%)(David M. Robertson et al. (2007), *Cancer Letters,* 249 (1):14-17). Therefore, more tumor markers for detecting and monitoring ovarian cancer are highly desired.

For example, inhibin has been investigated for use as a diagnostic marker for ovarian cencer (David M. Robertson et al. (2007), supra).

WO 99/57565 discloses methods for cancer diagnosis, and more particularly to the use of compounds that detect expression of OB-cadherin or N-cadherin for diagnosing and determining the metastatic potential of cancers such as breast, ovarian and prostate cancer, as well as leukemia.

U.S. Pat. No. 7,189,507 B2 discloses genes whose expression is up-regulated or down-regulated in ovarian cancer. Referring to Table 14A of the Specification of U.S. Pat. No. 7,189,507 B2, there is listed a gene that is identified to correspond to the gene deposited with Accession No. AF129085, which is Homo sapiens carboxy terminus of Hsp70-interacting protein (CHIP)[also known as STIP1 homology and U-box containing protein 1 (STUB1)] mRNA.

U.S. 2004/0096915 A1 discloses a method for the diagnosis, prognosis, and monitoring of ovarian cancer in a subject by detecting human kallikrein 6 (hK6) in a sample from the subject, preferably a serum sample or tumor tissue extract.

Despite of the aforesaid, many investigators endeavored to explore new biomarkers for ovarian cancers. The applicants surprisingly found form experiments that the levels of STIP1 in patients with ovarian cancers and endometriosis were significantly higher than those in normal controls, suggesting that STIP1 be useful as a biomarker for the detection of ovarian cancers and endometriosis.

SUMMARY OF THE INVENTION

Therefore, according to a first aspect, this invention provides a method for the detection or preliminary screening of a gynecological disease in a human subject, the gynecological disease being selected form ovarian cancers and endometriosis, the method comprising:

obtaining a biological sample from the human subject; and
    detecting the level of stress-induced phosphoprotein 1 (STIP1) in said biological sample, and
    comparing the detected level of STIP1 of said biological sample with that of a standard, the human subject being determined to have the gynecological disease if the detected level of STIP1 of said biological sample is higher than that of the standard.

In a second aspect, this invention provides a method for monitoring a gynecological disease in a human subject, the gynecological disease being selected form ovarian cancers and endometriosis, the method comprising:

periodically obtaining a biological sample from the human subject;
    detecting the level of STIP1 in said biological sample, and
    comparing the detected level of STIP1 of said biological sample with that of a standard, the human subject being determined to have the gynecological disease if the detected level of STIP1 of said biological sample is higher than that of the standard.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

Disease proteomics is a new discipline where proteomics is applied to better understand disease processes, to develop new biomarkers for diagnosis and early detection of disease, and to accelerate development of drugs (Sam Hanash (2003), *Nature*, 422(6928):226-232; Sam Hanash (2004), *Molecular & Cellular Proteomics*, 3(4):298-301).

A systemic search for potential biomarkers of solid cancer emphasized the comparison of the protein profiles of tumor interstitial fluids (TIF) and nonmalignant normal interstitial fluids (NIF)(Julio E. Celis et al. (2004), *Molecular & Cellular Proteomics*, 3(4):327-344). Rationale of this approach is that proteins in TIF and NIF readily enter circulation through the lymphatic system. Hence, unusual levels of proteins in TIF may be detected in peripheral blood as well and may serve as easily accessible tumor markers. This TIF versus NIF approach requires the qualitative and quantitative comparison of hundreds of sample pairs using 2D SDS-PAGE-based proteomics, the preparation of specific antibodies against putative markers for validation, as well as the analysis of the corresponding serum/plasma and other control samples for the presence of these markers (Julio E. Celis et al. 2005, FEBS J., 272(1):2-15).

In an attempt to identifying new tumor markers for ovarian cancers, the applicants used two-dimensional polyacrylamide gel electrophoresis (2D SDS-PAGE) to compare proteomes between tumor interstitial fluids of ovarian cancers and normal interstitial fluids of control ovaries and identified several differentially expressed proteins. The applicants' study revealed that stress-induced phosphoprotein 1 (STIP1) (GeneID 10963; HPRD 05454) was differentially expressed between ovarian cancers and normal ovaries as determined by western blot analysis and immunohistochemistry. The applicants further developed an ELISA for measuring serum levels of STIP1. Based on receiver operating characteristics (ROC) curve analysis of serum levels of STIP1 in ovarian cancer patients and controls, it was suggested that the discriminative capacity of STIP1 for ovarian cancer was comparable to that of CA125. To the applicants' surprise, similar results were also obtained for patients with endometriosis via ELISA and immunohistochemistry analyses. Given the fact that STIP1 and CA125 function in distinct biological processes, increased levels of STIP1 and CA125 may be used together as complementary biomarkers for ovarian cancer and for endometriosis.

Accordingly, this invention provides a method for the detection or preliminary screening of a gynecological disease in a human subject, the gynecological disease being selected form ovarian cancers and endometriosis, the method comprising:

obtaining a biological sample from the human subject;
detecting the level of stress-induced phosphoprotein 1 (STIP1) in said biological sample, and
comparing the detected level of STIP1 of said biological sample with that of a standard, the human subject being determined to have the gynecological disease if the detected level of STIP1 of said biological sample is higher than that of the standard.

This invention also provides a method for monitoring a gynecological disease in a human subject, the gynecological disease being selected form ovarian cancers and endometriosis, the method comprising:

periodically obtaining a biological sample from the human subject;
detecting the level of STIP1 in said biological sample, and
comparing the detected level of STIP1 of said biological sample with that of a standard, the human subject being determined to have the gynecological disease if the detected level of STIP1 of said biological sample is higher than that of the standard.

When the gynecological disease is an ovarian cancer, the biological sample may be selected from blood, serum, plasma, ovarian tissue, interstitial fluid prepared from ovarian tissue, and combinations thereof. When the biological sample is ovarian tissue or interstitial fluid prepared therefrom, the ovarian tissue may be taken from the subject via a surgical operation, biopsy or laparoscopy/peritoneoscopy.

In a preferred embodiment of this invention, the biological sample is serum. In another preferred embodiment of this invention, the biological sample is ovarian tissue. In a further preferred embodiment of this invention, the biological sample is interstitial fluid prepared from ovarian tissue.

According to this invention, the level of STIP1 of the standard may correspond to levels obtained for other samples taken from the subject, or samples taken from control subjects (healthy subjects and/or subjects with benign ovarian tumor).

The methods of this invention as described above are useful in the detection of various ovarian cancers, including, but not limited to: serous papillary carcinoma, serous papillary cystadenocarcinoma, adenocarcinoma, moderately differentiated adenocarcinoma, poorly differentiated adenocarcinoma, and endometrioid carcinoma.

According to this invention, the gynecological disease may be endometriosis, including endometriosis interna (also known as adenomyosis), and endometriosis externa (currently referred to as "endometriosis"), such as endometriotic cyst (also known as endometrioma).

When the the gynecological disease is endometriosis, the biological sample may be selected from blood, serum, plasma, endometriotic tissue or ectopic endometrial tissue, and combinations thereof. In a preferred embodiment of this invention, the biological sample is serum. According to this invention, the level of STIP1 of the standard may correspond to levels obtained for other samples taken from the subject, or samples taken from control subjects (healthy subjects and/or subjects with benign ovarian tumor).

The level of STIP1 may be measured by any means known to those skilled in the art. According to this invention, it is generally preferred to use antibodies, or antibody equivalents, to detect the level of STIP1 in the biological sample. However, other methods for detecting the level of STIP1 can also be used, such as measuring STIP1 expression by analysis of mRNA transcripts.

In a preferred embodiment of this invention, the levels of STIP1 expression are measured by quantifying STIP1 protein using at least one of the following methodologies: gel electrophoresis, Western blotting, enzyme immunoassay such as enzyme linked immunosorbent assay (ELISA), radioimmunoassay, immunohistochemistry (IHC), proteomics and the like.

In a preferred embodiment of this invention, quantifying STIP1 protein is conducted using an antibody-based binding moiety that specifically binds STIP1 protein. In a more preferred embodiment of this invention, the antibody-based binding moiety is labeled with a detectable label selected from the group consisting of a radioactive label, a hapten label, a fluorescent label, and an enzymatic label.

The term "antibody-based binding moiety" or "antibody" includes immunoglobulin molecules and immunologically active determinants of immunoglobulin molecules, e.g., molecules that contain an antigen-binding site that specifically binds (immunoreacts with) to STIP1 protein. The term "antibody-based binding moiety" is intended to include whole antibodies of any isotype (e.g., IgG, IgA, IgM, IgE, etc.), and includes fragments thereof that are also specifically reactive with STIP1 protein.

Antibodies can be fragmented using conventional techniques. Thus, the term fragment thereof includes segments of proteolytically-cleaved or recombinantly-prepared portions of an antibody molecule that are capable of selectively reacting with a certain protein. Non-limiting examples of such proteolytic and/or recombinant fragments include Fab, F(ab') 2, Fab', Fv, dabs and single chain antibodies (scFv) containing a VL and VH domain joined by a peptide linker. The scFv's may be covalently or non-covalently linked to form antibodies having two or more binding sites.

The term "antibody-based binding moiety" includes polyclonal, monoclonal, or other purified preparations of antibodies and recombinant antibodies. The term "antibody-based binding moiety" is further intended to include humanized antibodies, bi-specific antibodies, and chimeric molecules having at least one antigen-binding determinant derived from an antibody molecule.

In a preferred embodiment, the antibody-based binding moiety is detectably labeled. As used herein, "Labeled antibody" includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the methods of the invention that use antibody-based binding moieties for the detection of STIP1, the levels of STIP1 protein present in the biological sample correlate to the intensity of the signal emitted from the detectably labeled antibody.

In one preferred embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, β-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audoradiography. Isotopes which are particularly useful for the purpose of the present invention are $^3$H, $^{31}$P, $^{35}$S, $^{14}$C, and $^{125}$I.

It is also possible to label an antibody with a fluorescent compound. When the fluorescently labeled antibody is exposed to light of the proper wavelength, its presence can be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine. An antibody can also be detectably labeled using fluorescence emitting metals such as $^{152}$Eu, or others of the lanthanide series. These metals can be attached to the antibody using metal-chelating groups such as diethylenetriaminepentaacetic acid (DTPA) or ethylenediaminetetraacetic acid (EDTA). An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, the quantity or level of STIP1 protein can be detected by immunoassays, such as enzyme-linked immunoabsorbant assay (ELISA), radioimmunoassay (RIA), Immunoradiometric assay (IRMA), Western blotting, or immunohistochemistry. Antibody arrays or protein chips can also be employed.

Proteomics typically includes the following steps: (1) separation of individual proteins in a sample by 2-D gel electrophoresis (2D PAGE); (2) identification of the individual proteins recovered from the gel, e.g. by mass spectrometry or N-terminal sequencing; and (3) analysis of the data using bioinformatics. Proteomics methods are valuable supplements to other methods of gene expression profiling, and can be used, alone or in combination with other methods, to detect the products of the biomarker of HCC according to this invention.

Mass spectrometry methods are well known in the art and have been used to quantify and/or identify biomolecules, such as proteins. Therefore, in the method of this invention, STIP1 protein may also be detected using mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, EST-MS/MS, etc.).

To enhance detection sensitivity and specificity, the methods of this invention as described above may further comprise the steps of parallelly detecting the level of CA125 in said biological sample, and comparing the detected level of CA125 of said biological sample with that of a standard. Detection of CA125 may be performed as previously described.

This invention also contemplates the manufacture of diagnosis kits for the detection, preliminary screening or monitoring of ovarian cancer and endometriosis in a human subject, which comprises means for identifying the presence of STIP1 protein or quantifying the level of STIP1 protein, and instructions to use said means in a method as described above.

EXAMPLES

The present invention will be described in more detail with reference to the following examples, which are given for the purpose of illustration only and are not intended to limit the scope of the present invention.

Study Design

The experimental design and the involvement of human subjects in the study of this invention received approval from the ethical committee of Chang Gung Memorial Hospital. In addition, informed consent was obtained from each of the human subjects studied in this invention for the donation of their ovarian tissues.

Tumorous ovarian tissues and normal ovarian tissues were obtained during surgery from subjects suspected to have ovarian malignancies and those having benign gynecological conditions such as adenomyosis or myoma uteri, respectively.

Immediately after resection, a part of the resected ovarian tissue (either tumorous or normal) was subjected to pathological examination. For the remaining part of the resected ovarian tissue, a piece at a size of $1\times1\times1$ cm$^3$ was taken to the laboratory for the procedures as outlined in FIG. 1. A half of the piece of ovarian tissue (around $0.5\times0.5\times0.5$ cm$^3$) was used to prepare tumor interstitial fluid (TIF) or normal interstitial fluid (NIF). The other half of the piece of ovarian tissue was subjected to cryosection, followed by hematoxylin and eosin staining, so as to verify that the ovarian tissue contained more than 80% of cancer cells. The left resected ovarian tissue was snap frozen in liquid nitrogen and stored at $-80°$ C. TIF samples, NIF samples, cryosection samples and frozen tissue samples were prospectively collected. However, a TIF sample was enrolled into the study of this invention for the two-dimensional gel electrophoresis analysis only after the pathology report confirmed that the resected ovarian tissue was determined to be serous epithelial ovarian cancer.

Sera from patients with ovarian cancer or endometriosis, or sera of normal individuals as used in the study of this invention were the leftover specimens stored under $-20°$ C. at the Department of Clinical pathology of Chang Gung Memorial Hospital.

Reagents, Cell Lines, and Tissue Arrays

The majority of the chemicals used in the study of this invention were purchased from Sigma-Aldrich (St Louis, Kans.). Exceptions included: acetonitrile (ACN) (Merck, Whitehouse Station, N.J.), methanol (Merck), formalin (Riedel-deHaen, Seeize, Germany), AgNO$_3$ (AppliChem GmbH, Gatersleben, Germany), dithiothreitol (AppliChem, Darmstadt, Germany), iodoacetamide (AppliChem), trypsin (Promega, Madison, Wis.), and peptide calibration standard for mass spectrometry (Bruker Daltonics, Bremen, Germany). Concerning the used human ovarian cancer cell lines, TOV112D, TOV21G, SKOV3, MDAH2774, and ES2 were obtained from ATCC (American Type Culture Collection), whereas BR and BG1 were previously reported (Tzu-Hao Wang et al. (1998), *J. Biol. Chem.*, 273(9):4928-36; Tzu-Hao Wang et al. (1999), *J. Biol. Chem.*, 274(12):8208-16).

Cancer cells were cultured in DMEM/F12 supplemented with 10% fetal bovine serum and antibiotics at 37° C. with 5% CO$_2$. In an in vitro experiment, MDAH2774 cells were cultured in a serum-free medium for 24 hrs and then subjected to a 5-min treatment using a serum-free DMEM/F12 containing 200 nM recombinant human STIP1 (Abnova, Taiwan). Cell lysates were analyzed for extracellular response kinase (ERK) activations with specific antibodies (Santa Cruz). Tissue arrays containing human ovarian tumors were obtained from SuperBioChips Laboratory (Seoul, Korea).

Preparation of Tumor Interstitial Fluid (TIF) or Normal Interstitial Fluid (NIF)

Immediately after surgery, a piece of the resected tumorous/normal ovarian tissue ($0.5\times0.5\times0.5$ cm$^3$) was minced with sharp scissors, weighed, and rinsed with iced phosphate-buffered saline (PBS), followed by incubation with 800 µL PBS at 37° C. for 1 hr. After spinning at 8,000×g at 4° C. for 20 min, the collected supernatant was desalted with the Bio-Rad Clean-up kit and rehydrated with a rehydration buffer (8M urea, 4% CHAPS, without bromophenol blue). Each TIF or NIF thus obtained was subjected to a protein concentration quantification using the BioRad Bradford protein assay and then stored in aliquots of 100 µL/tube at $-80°$ C. until assayed.

Two-dimensional (2D) Gel Electrophoresis and Image Analysis

Except for minor modifications, the experimental procedures were performed as previously reported (Sen-Yung Hsieh et al. (2006), *Proteomics*, 6(19):5322-31).

Briefly, 400 µg of TIF or NIF protein was added with 2.5 mg DTT and 3.3 µL Biolyte (pH 3-10) and the rehydration buffer to a final volume of 330 µL, and the resultant solution was applied to a 17-cm IPG strip (linear pH 5-8, BioRad). The first dimensional electrophoresis was run using a BioRad Protein IEF Cell with the following program: 20° C., 50 mA/strip for 12 hrs; 100 V rapid for 30 min; 500 V slow for 30 min; 1000 V slow for 30 min; 5000V slow for 30 min; 8000 V slow for 1 hr; 58000 V-h rapid; and 250 V rapid for 24 hrs.

Thereafter, each IPG strip was reduced using 3 mL of an equilibrium buffer (6M urea, 30% glycerol, 30 mM Tris (pH 8.8), 0.005% bromophenol blue, 70 mM SDS) containing 0.06 g DTT in dark for 20 min, alkylated with 3 mL of an equilibrium buffer containing 0.075 g IAA in dark for 20 min, and then applied to the second dimensional electrophoresis using a 12.5% 2D polyacrylamide gel. The 2nd dimensional electrophoretic program was set as follows: 1000 V, 15 mA/gel, and 250 W.

After fixed in a fix/destain solution (10% methanol/7% acetic acid in water) for 2 hrs, the 2D gel was stained using a SYPRO Ruby solution (Molecular Probes, Eugene, Oreg.) for 16 hrs at room temperature. Thereafter, the 2D gel was immersed in the fix/destain solution with shaking for 2 hrs, followed by rinsing with d.d. $H_2O$ for 10 min twice.

The SYPRO Ruby-stained 2D gels were scanned using a ProXPress 2D scanner (PerkinElmer, Shelton, Conn.). Images were analyzed with the Progenesis Workstation software (Nonlinear Dynamics, Durham, N.C.), in which a gel created by the Progenesis Workstation software and containing the most abundant protein spots was used as the reference image (R).

In Gel Enzymatic Digestion and Mass Spectrometry

Except for minor modifications, the experimental procedures were performed as previously reported (Sen-Yung Hsieh et al. (2006), supra).

The protein spots of interest were manually excised from the SYPRO Ruby-stained 2D gels, destained using 25 mM $Na_2CO_3$ in 100% ACN, and dried in a SpeedVac concentrator. Each of the protein spots thus collected was subjected to in-gel digestion with trypsin (Promega, Madison, Wis.; at 5 ng/mL)[20 ng/μL, in 25 mM $NH_4HCO_3$ (pH 7.8)] at 37° C. overnight. The resultant tryptic peptides were then extracted from the gel piece using 2 μL of 1% TFA with vortexing for 5 min, followed by sonication for 10 min three times. The crude digest mixture for each protein spot was concentrated and desalted and mixed with a matrix solution (1 mg of CHCA/mL in 70% ACN and 0.1% TFA) for MALDI-TOF MS and MS/MS analyses. To identify the protein present in each protein spot analyzed, both of the acquired MS and MS/MS spectra were searched against the NCBI database using the MASCOT software (Matrix Science Ltd., London, UK; www.matrixscience.com). The MALDI-TOF MS resolution for the peptides was around 20,000, and the mass accuracy was 0.01-0.02 Da. The MS/MS resolution was around 6,000.

Western Blot Analyses and Data Normalization

Except for minor modifications, the western blot analysis and the preparation of cell lysates from cancer cell lines were performed as previously reported (T-H Wang et al. (2006), Oncogene, 25:4857-66).

After protein quantification with the Bradford assay, 70 μg protein of each TIF and NIF was separated with a 10% SDS-polyacrylamide gel, followed by transferring to a nitrocellulose (NC) membrane (Amersham Bioscience, Piscataway, N.J.). The NC membrane were stained with Ponceau S solution (0.2% Ponceau S in 10% acetic acid) for 10 min, washed with water at room temperature for 5 min. After the nitrocellulose membrane were stained with Ponceau S, the protein content of the NC membrane was digitalized by scanning with a high-resolution flatbed color scanner (Hewlett-Packard) and analyzed with the UN-SCAN-IT software (Silk Scientific, Orem, Utah).

After removal of Ponceau S, the NC membrane was subjected to antibody probing using anti-STIP1, anti-TPI1, anti-UCHL1, anti-LAP3, anti-MACF1 (all purchased from Abnova Corporation, Taipei, Taiwan), and anti-cytokeratin 16 (Acris, Germany) as primary antibodies, in conjunction with corresponding horseradish peroxidase conjugated second antibodies (Santa Cruz). Bounded antibodies were visualized by enhanced chemiluminescence using the Pierce ECL system (Pierce, Rockford, Ill.).

To compare STIP1 levels in various human ovarian cancer cell lines, densitometric data of STIP1 were normalized with beta actin levels in the corresponding specimens. For the Western blot analysis of ERK activation, densitometric results of phosphor-ERK (SantaCruz) were normalized with total ERK levels (Santa Cruz).

Because the TIF samples and the NIF samples as tested herein were secreted from freshly resected tumorous ovarian tissues and normal ovarian tissues, respectively, these samples might not contain intracellular beta actin therein. Therefore, instead of using the level of beta actin in each sample to normalize the protein input in each lane, the amount of protein input in each lane was quantified by the whole intensity of each lane using the UN-SCAN-IT software. After the protein bands on a Western blot were quantified in terms of correct molecular weights using the UN-SCAN-IT software, the relative intensity of a target protein (e.g., STIP1) in each lane was normalized by the total protein intensity of each lane as determined by Ponceau S staining.

Enzyme-linked Immunosorbent Assay (EUSA)

The experimental procedures were performed as previously reported (Tzu-Hao Wang et al. (2006), Fertility and Sterility, 86(5): 1392-1401).

In all ELISA assays, tetramethylbenzidine was used as the substrate of peroxidase, and color intensities were detected at 450 nm using a spectrometer (Wallac 1420 VICTOR$^2$, PerkinElmer, Waltham, Mass.).

Human transferrin levels in the TIF and NIF samples were measured using a commercial ELISA kit (Alpha Diagnostic, San Antonio, Tex.). Prior to measurement, the TIF and NIF samples were diluted to 1:500 in PBS. The minimum detection limit of this assay was 50 ng/mL. The intraassay coefficients of variance (CVs) were 2.2% at 115 ng/mL and 8% at 518 ng/mL (n=10), respectively. The interassay CVs were 8.3% at 108 ng/mL and 6.2% at 499 ng/mL (n=5), respectively.

Human BDNF levels in the TIF and NIF samples were measured using a commercial kit (R&D, Minneapolis, Minn.) with a minimal detection limit of 20 pg/ml. The intraassay CVs for the BDNF ELISA were 5% at 476 pg/mL and 6.2% at 2175 pg/mL (n=6), respectively, whilst the interassay CVs were 11.3% at 528 pg/mL and 8.1% at 2287 pg/mL (n=6), respectively.

Human serum levels of CA125 were measured using a commercial Abbott Axsym system (Abbott Park, Ill.) with a detection sensitivity at 2 U/ml. The intraassay CVs and the inter-assay CVs were 16% (n=6) and 8.1% (n=20) at 8.81 U/ml, respectively, and were 5.87% (n=6) and 2.13% (n=20) at 44.37 U/ml, respectively.

The applicants developed an ELISA to determine serum levels of STIP1 using a chicken anti-human STIP1 polyclonal antibody (Abcam Laboratories, Cambridge, UK) as the capture antibody that was coated on 96-well plates (Nunc A/S, Roskilde, Denmark). Both human STIP1 recombinant protein and a mouse anti-human STIP1 monoclonal antibody were purchased from Abnova Corporation (Taipei, Taiwan). An HRP-conjugated sheep anti-mouse IgG antibody was purchased from Sigma-Aldrich (St Louis, Mo.), and the peroxidase substrate tetramethylbenzidine was from Bethyl Laboratories (Montgomery, Tex.). Cell lysates of the BR cells (a human ovarian cancer cell line) at both high and low concentrations were used for analyzing the intraassay and interassay CVs.

Immunohistochemistry (IHC)

Using procedures that were previously reported (Angel Chao et al. (2006), *Int. J. Cancer*, 119(1):91-98), the applicants conducted IHC studies on cryosection samples of human tumorous ovarian tissues and normal ovarian tissues, from which the TIF and NIF samples were derived, respectively. After fixed with paraformaldehyde, the sections were stained with a mouse anti-human STIP1 monoclonal antibody that was purchased from Abnova Corporation (Taipei, Taiwan), using an automated IHC stainer with the Ventana Basic DAB Detection kit (Tuscon, Ariz.) according to the manufacturer's protocol. Counterstaining was performed with hematoxylin.

The IHC studies were also performed on tissue arrays (SuperBioChips Laboratories, Seoul, Korea) that contained various human ovarian tumors. Slides with formalin-fixed, paraffin-embedded tissues sectioned at 4 μm thick were deparaffinized in xylene and rehydrated with a series of graded ethanol. The sections on the slides were then stained as described above.

Statistical Analysis

Using Statistica software (Statsoft, Tulsa, Okla.), the applicants applied the Kruskall-Wallis test (a nonparametric equivalent of ANOVA) and the Mann-Whitney U test (a nonparametric equivalent of the t-test) to analyze continuous variables, while using the paired t-test for ERK activation assays. We used a receiver-operating characteristic (ROC) curve analysis to evaluate the predictive values of STIP1 and CA125 (Mark H. Zweig (1993), i Clinical Chemistry, 39(6): 1345-1346). For all analyses, P values less than 0.05 were considered statistically significant.

Results

Figure 1:
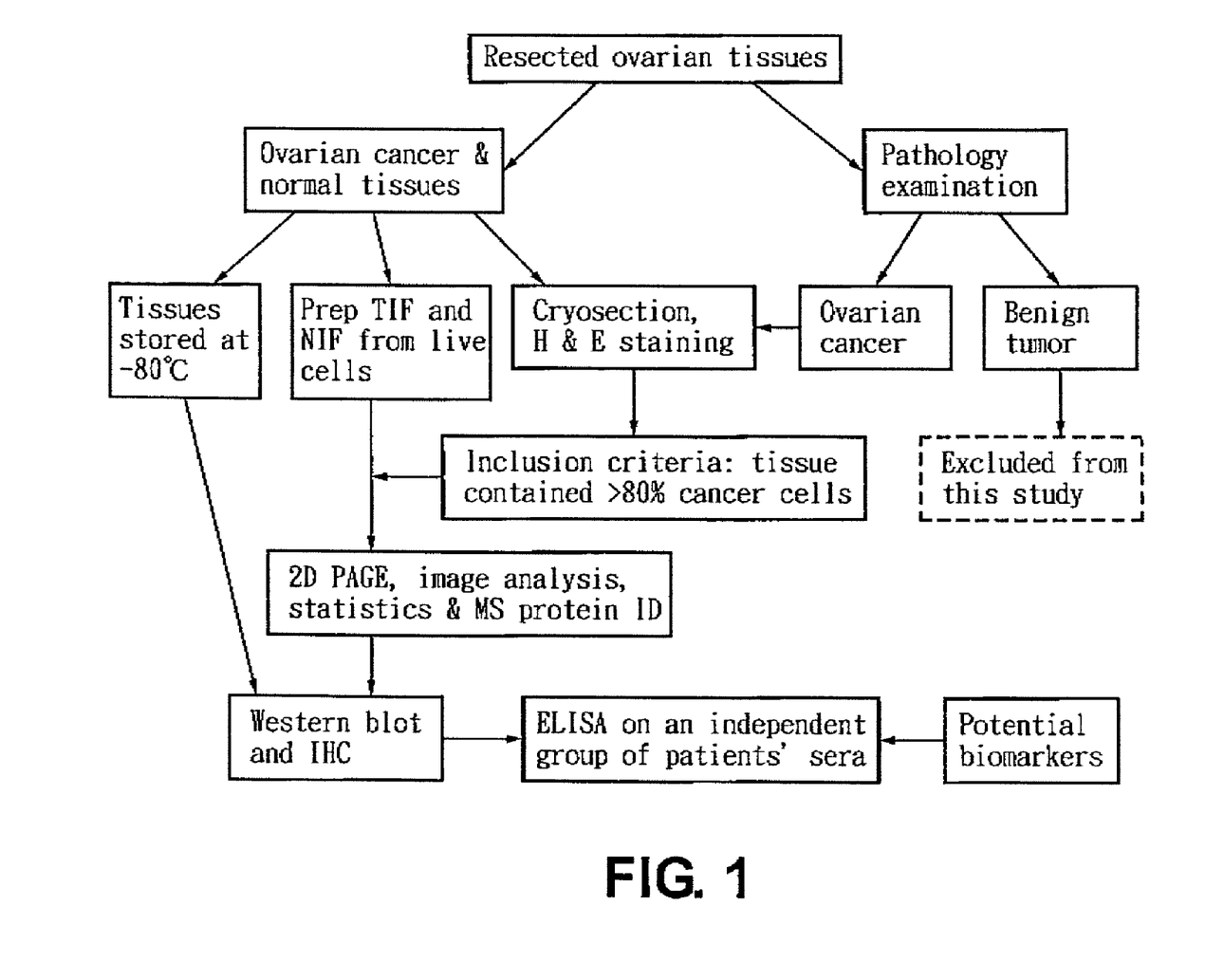
FIG. 1 shows the study design of this invention, in which a resected human ovarian tissue was used to prepare a tumor interstitial fluid (TIF) sample only when it was confirmed to be human serous ovarian cancer and it contained more than 80% of cancer cells.

Using the experimental design outlined in FIG. 1, nine ovarian cancer TIF samples and sixteen non-cancer ovarian NIF samples were enrolled in the study of this invention. All TIF samples were derived from serous epithelial carcinoma. There was no significant difference between TIFs and NIFs in terms of protein amount (P=0.53). The protein amounts of TIFs were 3965±1255 μg (mean±SE) and ranged from 590 to 13286 μg, whereas those for NIFs were 3166±628 μpg (mean±SE) and ranged from 525 to 8389 μg.

Figure 2:
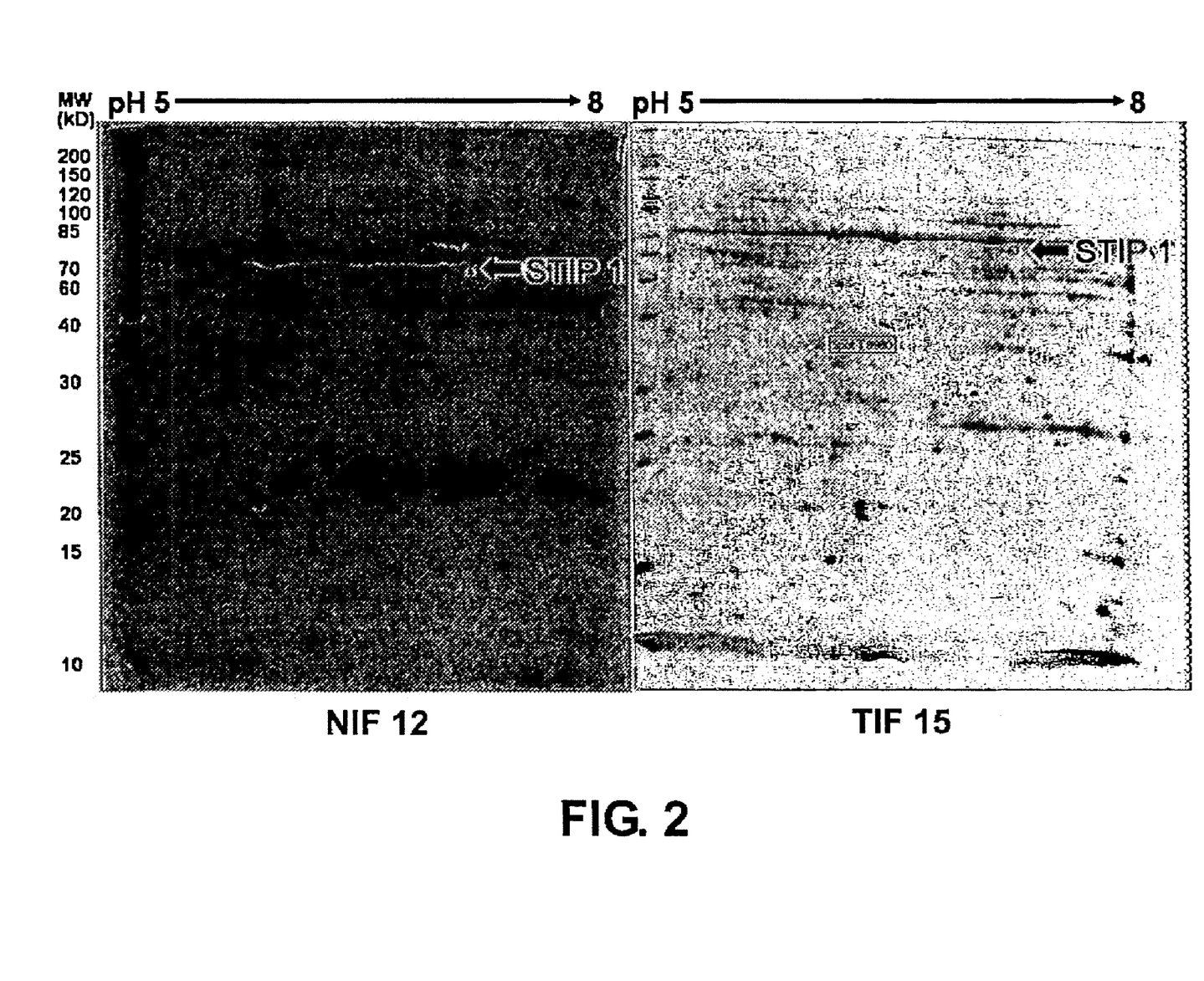
FIG. 2 shows a representative pair of SYPRO Ruby-stained 2D gels (pH 5 to 8) of TIF and NIF, in which a protein spot showing differential expression between TIF and NIF was identified to be STIP1.
Figure 3:
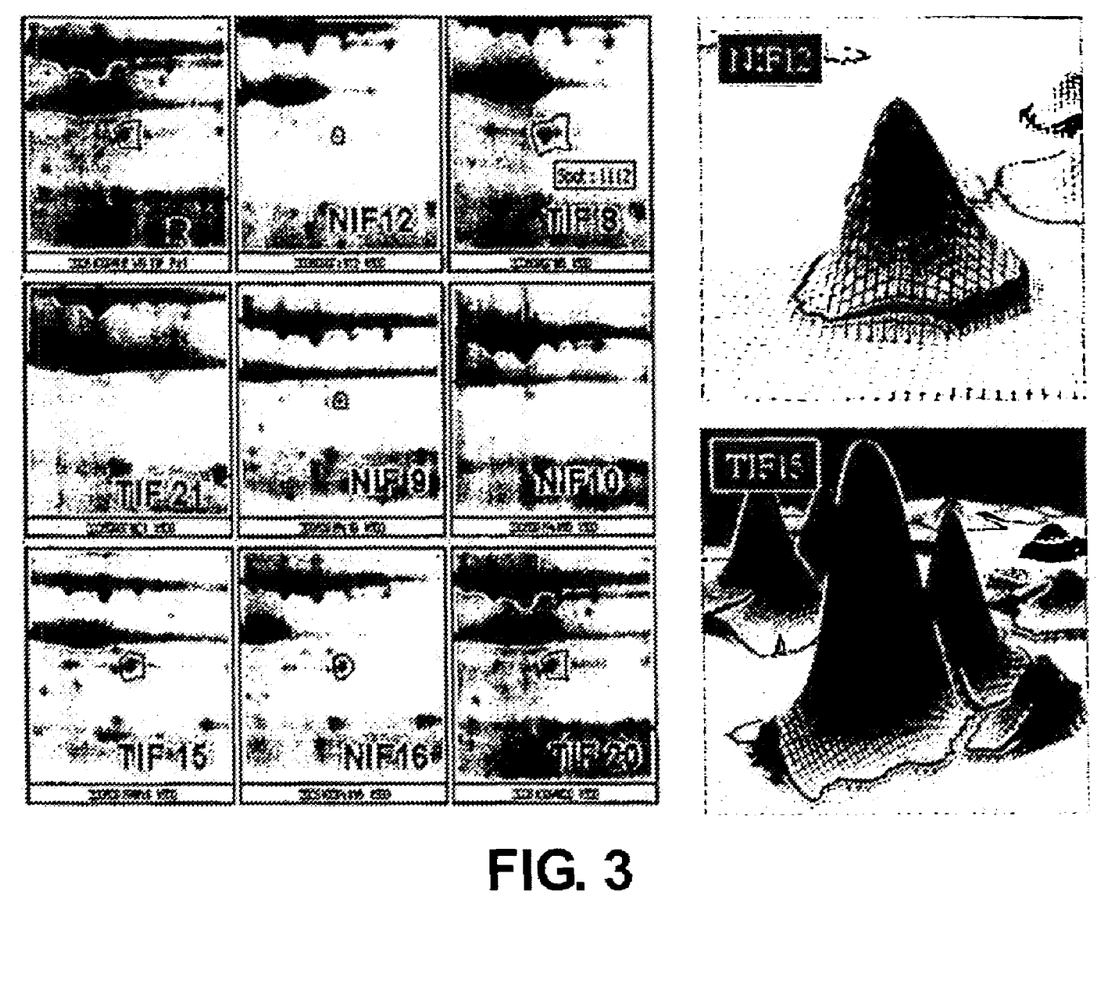
FIG. 3 shows the zoomed-in images of STIP1 spots in four pairs of SYPRO Ruby-stained 2D gels of TIFs and NIFs, in which a 2D gel, which was created by the Progenesis Workstation software (Nonlinear Dynamics, Durham, N.C.) and contained the most abundant protein spots, was used as a reference image (R)

The applicants analyzed four pairs of SYPRO Ruby-stained 2D gels (pH 5 to 8) of TIFs and NIFs to determine protein spots that were differentially expressed between TIFs and NIFs. FIG. 2 shows a representative pair of the 2D gels, in which a protein spot showing differential expression between TIF and NIF was identified to be STIP1. FIG. 3 shows the zoomed-in images of STIP1 spots in four pairs of SYPRO Ruby-stained 2D gels of TIFs and NIFs.

A total of 596 protein spots were analyzed statistically. Using P<0.05 as a significant threshold, 10 protein spots were identified to show different amounts between the TIF and NIF groups via the non-parametric Mann-Whitney U test. Using in-gel digestion and MALDI-TOF mass spectrometry, the applicants successfully identified six proteins that are higher in TIFs than in NIFs, i.e., stress-induced phosphoprotein-1 (STIP1), leucine aminopeptidase 3 (LAP3), type I keratin 16, macrophin 1 isoform 2 (MACF1), brainderived neurotrophic factor isoform b preproprotien (BDNF1), and triosephosphate isomerase 1 (TPI1), and two proteins that are lower in TIFs than in NIFs, i.e., ubiquitin carboxyl-terminal esterase L1 (UCHL1) and transferrin (Table 1).

Figure 4:
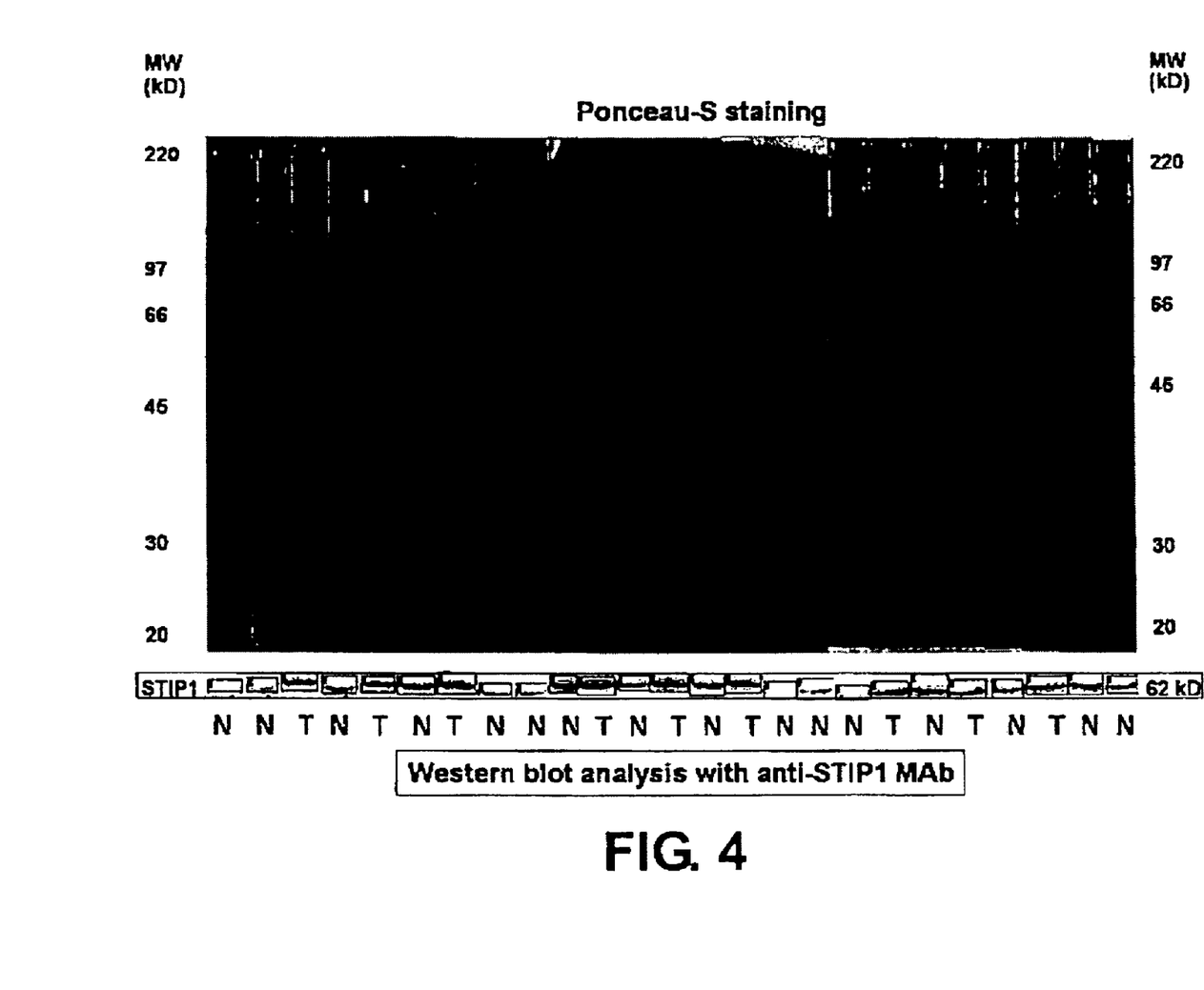
FIG. 4 shows that the STIP1 level was higher in TIF than in NIF of the human ovary as confirmed by Western blot analysis, in which twenty-five protein specimens were electrophoresed on three 10% SDS-polyacrylamide gels (9, 8, and 8 specimens for gels 1, 2, and 3, respectively), followed by transferring to three separate nitrocellulose membranes. After stained with Ponceau S (upper panel), the protein contents of the nitrocellulose membranes were digitalized by scanning and analyzed with the UN-SCAN-IT software (Silk Scientific, Orem, Utah). The intensity of STIP1 in each lane as determined by Western blot analysis (lower panel) was normalized with the total protein intensity of each lane as determined by Ponceau S staining, so that all 25 specimens could be compared with each other.

The differential levels of selected protein spots between TIFs and NIFs were further confirmed in 9 TIFs and 16 NIFs using Western blot analysis or ELISA (Table 1). An example of quantitative western blot analysis was shown in FIG. 4. Twenty-five protein specimens were electrophoresed on three 10% SDS-polyacrylamide gels (9, 8, and 8 specimens for gels 1, 2, and 3, respectively), followed by transferring to three separate nitrocellulose membranes. The total amount of protein input in each lane was determined by Ponceau S staining (upper panel), which was used to normalize the level of the 62-kD STIP1 band (lower panel). After normalization, all results were analyzed with the Mann-Whitney U test. Except for the ambiguous results of type I keratin 16 and for the extremely large size of MACF1 (529 kDa), the applicants analyzed six proteins and verified the significant differences of STIP1, TPI1 and transferrin levels between TIFs and NIFs (Table 1).

Figure 5:
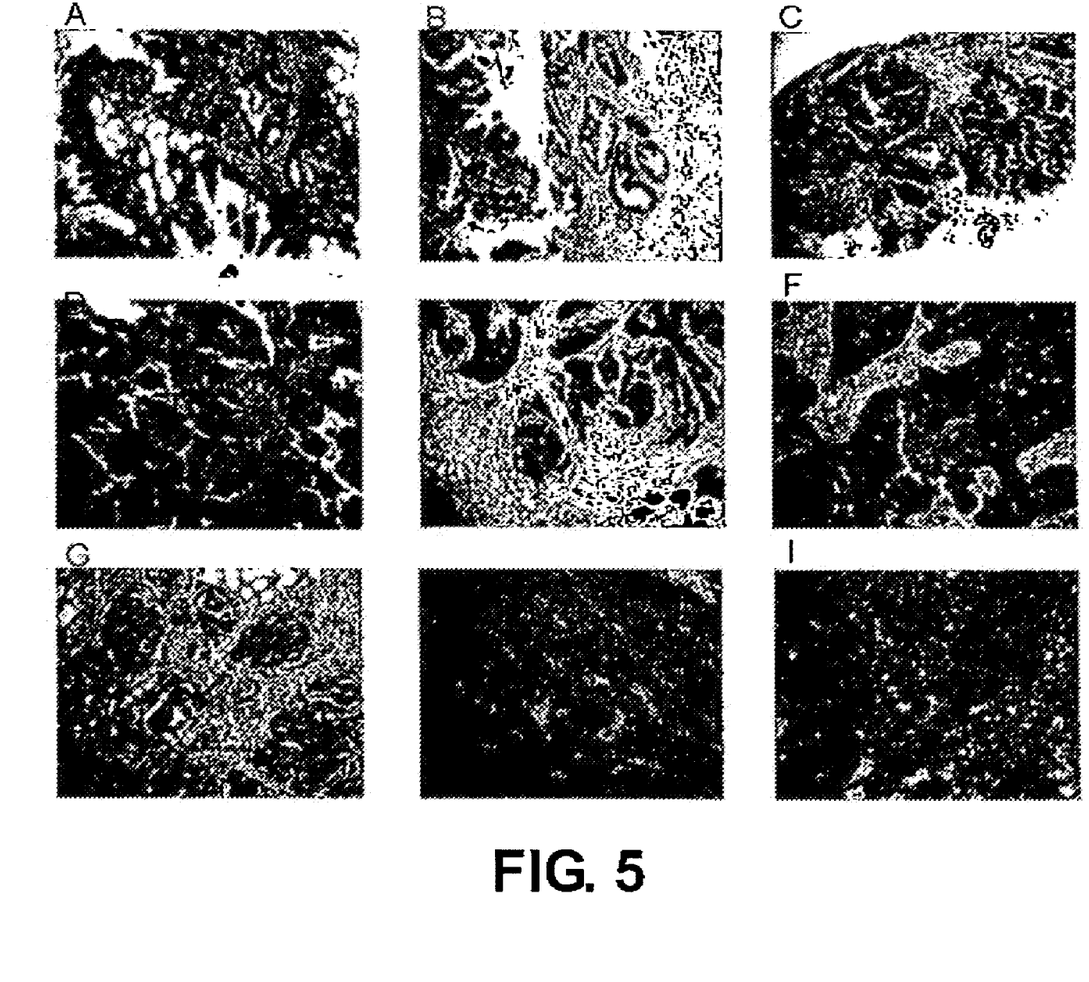
FIG. 5 shows the immunohistochemistry of STIP1 in various types of human ovarian cancers (panels A to G) and benign tumors (panels H to I), in which STIP1 was specifically recognized by an anti-STIP1 monoclonal antibody and represented as brown color. Counterstaining was performed with hematoxylin. The objective lens was 10X. Panel A, serous papillary carcinoma; panel B, serous papillary cystadenocarcinoma; panel C, adenocarcinoma; panel D, moderately differentiated adenocarcinoma; panel E, poorly differentiated adenocarcinoma; panel F, endometrioid carcinoma; panel G, endometrioid carcinoma; panel H, fibroma; and panel I, fibrothecoma. Notably, no immunostaining of STIP1 was noted in benign fibroma and fibrothecoma.

Using immunohistochemistry analysis, it was found that increased intensities of STIP1 immunoreactivities in cryosection samples of human ovarian cancer tissues, but not in normal ovaries (data not shown). It was also found that there are specific expression of STIP1 in paraffin-embedded human ovarian cancers, including serous adenocarcinoma and endometrioid carcinoma, but not in benign fibroma and fibrothecoma (FIG. 5). To the applicants' surprise, similar results were obtained for endometriosis patients via immunohistochemistry analysis (data not shown).

TABLE 1

Differentially expressed proteins between TIF and NIF (identified as P value <0.05 with Mann-Whitney U test)

| Name | Accession Number | Theoretical PI/MW (kD) | MASCOT score | Original results from 4 TIFs and 4 NITs | TIF levels[1] (n = 9) | NIF levels[1] (n = 16) | P values | Confirmed by |
|---|---|---|---|---|---|---|---|---|
| STIP1 | gi5803181 | 6.40/62.60 | 184 | TIF > NIF | 1.35 ± 0.14 | 0.79 ± 0.11 | P < 0.005 | Western blot |
| LAP3 | gi4335941 | 7.58/56.01 | 150 | TIF > NIF | 0.94 ± 0.20 | 1.03 ± 0.15 | NS (P = 0.72) | Western blot |
| Type 1 Keratin 16 | gi1195531 | 4.99/51.21 | 75 | TIF > NIF | NA | NA | NA | Not done |
| MACF1 | gi17426164 | 5.04/529.39 | 76 | TIF > NIF | NA | NA | NA | Not done |
| BDNF[2] | gi25306235 | 9.21/28.85 | 67 | TIF > NIF | 21.66 ± 12.03 | 20.36 ± 6.97 | NS (P = 0.92) | ELISA[2] |
| TPI1 | gi999892 | 6.51/26.52 | 125 | TIF > NIF | 1.27 ± 0.11 | 0.82 ± 0.08 | P < 0.005 | Western blot |
| UCHL 1 | gi21361091 | 5.33/24.81 | 91 | TIF < NIF | 0.84 ± 0.27 | 1.06 ± 0.21 | NS (P = 0.53) | Western blot |
| Transferrin[3] | gi4557871 | 6.81/77.00 | 113 | TIF < NIF | 22.76 ± 3.62 | 34/45 ± 2.72 | P < 0.05 | ELISA[3] |

[1]Data are expressed as mean ± standard error (SE).
[2]BDNF results of TIF and NIF were normalized by the protein concentration of each specimen and thereby expressed as pg/mg.
[3]Transferrin results of TIF and NIF were normalized by the protein concentration of each specimen and thereby expressed as ng/mg.

Figure 6:
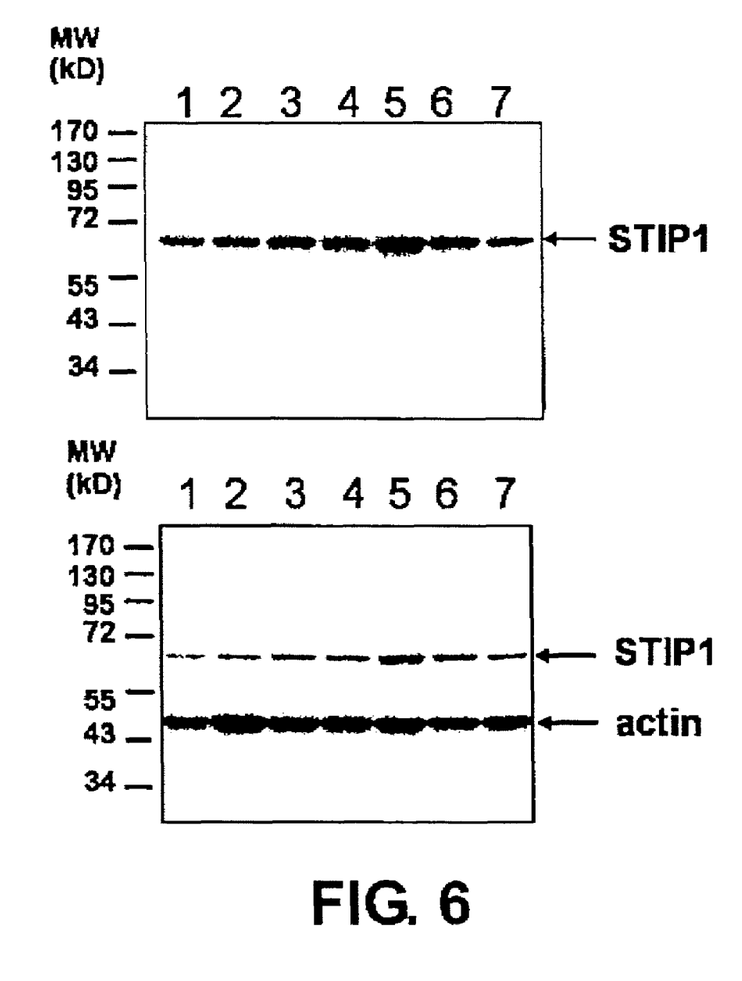
FIG. 6 shows the Western blot analysis of STIP1 in various human ovarian cancer cell lines. About 75 µg of cell lysates for each ovarian cancer cell line were used for western blot analyses, in which lane 1, TOV112D; lane 2, TOV21G; lane 3, SKOV3; lane 4, MDAH2774; lane 5, ES2; lane 6, BR; and lane 7, BG1.

FIG. 6 shows the Western blot analyses on various human ovarian cancer cell lines, in which the relative levels of STIP1 (normalized by beta actin levels) were highest in BR (1.33), followed by ES2 (1.28), MDAH2774 (1.07), SKOV3 (1.05), TOV112D (0.87), BG1 (0.76), and lowest in TOV21G (0.69). Therefore, the applicants prepared two different concentrations of BR ovarian cancer cell lysates for use as quality controls in the development of ELISA for STIP1. The detection sensitivity of the STIP1 ELISA was 2 ng/ml. Intra-assay coefficients of variance (CVs) of the STIP1 ELISA were from 6.73 to 17% in 4 assays (n=6 in each assay) at 114.88 ng/ml, and from 4.28 to 11% in 4 assays (n=6 in each assay) at 30.21 ng/ml (Table 2). Inter-assay CVs were 12.18% at 114.88 ng/ml concentration (n=4) and 13.7% at 30.21 ng/ml (n=4) (Table 2).

TABLE 2

Coefficients of variance (CV) of STIP1 ELISA

|  | High BR control | Low BR control |
|---|---|---|
| 1st CV % (mean ± SD) | 17.00% (123.23 ± 27.89) | 11.00% (34.49 ± 3.94) |
| 2nd CV % (mean ± SD) | 12.00% (93.89 ± 11.36) | 8.00% (24.86 ± 2.15) |
| 3rd CV % (mean ± SD) | 8.09% 120.12 ± 9.73) | 8.01% (29.31 ± 2.34) |
| 4th CV % (mean ± SD) | 6.73% (122.29 ± 8.23) | 4.28% (32.17 ± 1.38) |

STIP1 ELISA inter assay CV %: 12.18% at 114.88 ng/ml (n = 4) 13.7% at 30.21 ng/ml (n = 4)

Figure 7:
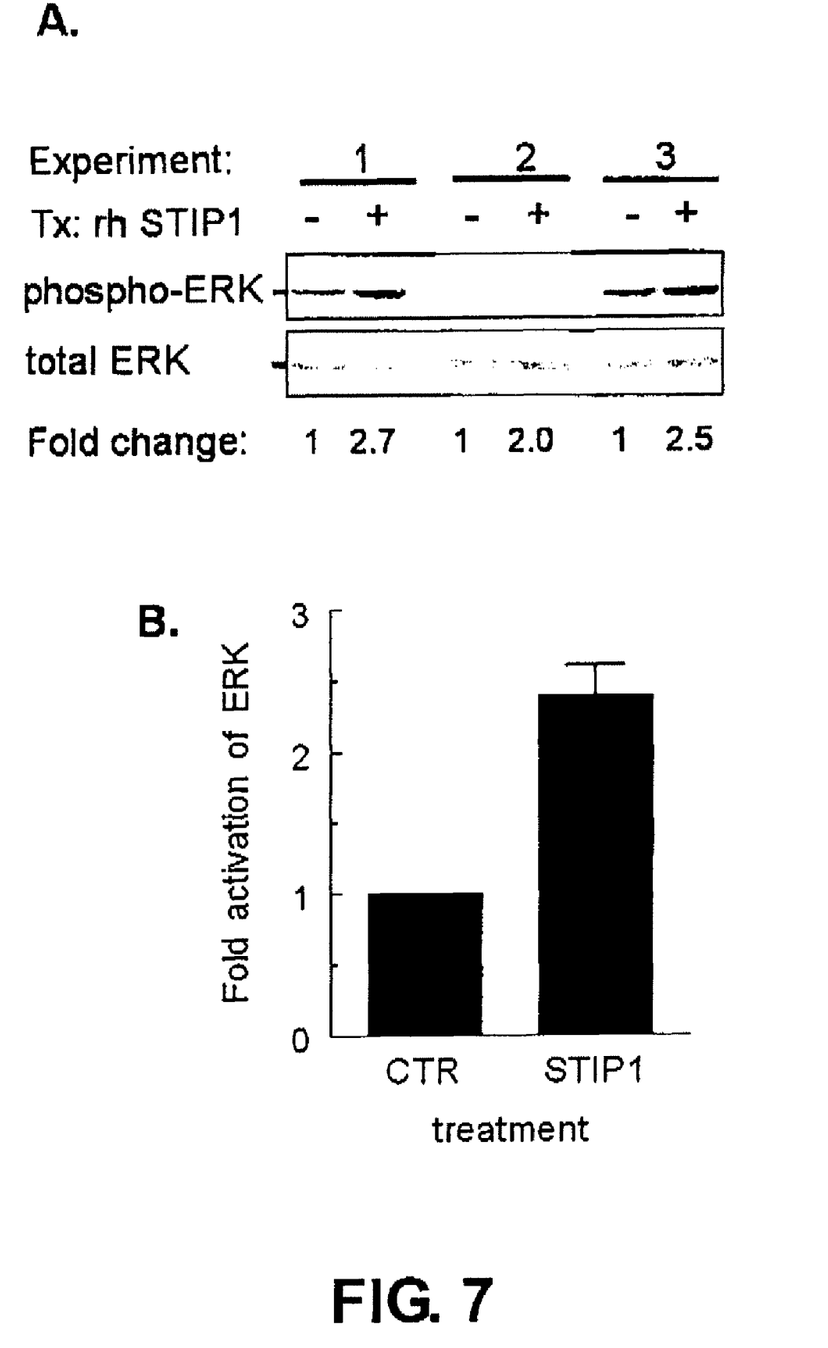
FIG. 7 shows that an in vitro treatment of recombinant human STIP1 to a human ovarian cancer cell line MDAH2774 significantly induced about 2.4 fold of ERK phosphorylation in MDAH2774 cells (experiments being carried out in triplicate, $P<0.05$); and, FIG. 8 shows that STIP1 and CA125 are differentially expressed amongst the ovarian cancer group, the endometriosis group and the normal control group, in which panel A, a comparison of serum levels of STIP1 and CA125 amongst the ovarian cancer group (Ov Ca), the endometriosis group (EMS) and the normal control group (NC); panel B, a comparison of serum levels of STIP1 and CA125 between the ovarian cancer group (Ov Ca) and the non-cancer group (Non-Ca, a combination of the endometriosis group and the normal control group); and panel C, a receiver operating characteristics (ROC) curve analysis for STIP1 and CA125.

To determine whether STIP1 had stimulatory effect(s) in ovarian cancer as previously reported in glioblastoma cells (Tatiana A. Americo et al. (2007), Biochem. Biophys. Res. Commun., 358(2):620-625), MDAH2774 cells (an ovarian cancer cell line) were cultured in serum-free medium for 24 hrs, followed by incubation with serum-free DMEM/F12 containing 200 nM recombinant human STIP1 (Abnova Inc., Taiwan) for 5 min. Cell lysates were analyzed for ERK activations with phosphorylated ERK-specific antibodies (Santa Cruz). As shown in FIG. 7, in vitro treatment with recombinant human STIP1 significantly induced about 2.4 fold of ERK phosphorylation in MDAH2774 cells ($P<0.05$).

To evaluate whether STIP1 could be used as a blood biomarker for ovarian cancer and endometriosis, the applicants developed an ELISA with the specifications are listed in Table 2 to analyze the serum levels of STIP1 with ELISA, with the serum levels of CA125 being assayed by a commercial Abbott Axsym system (Abbott Park, Ill.).

Figure 8:
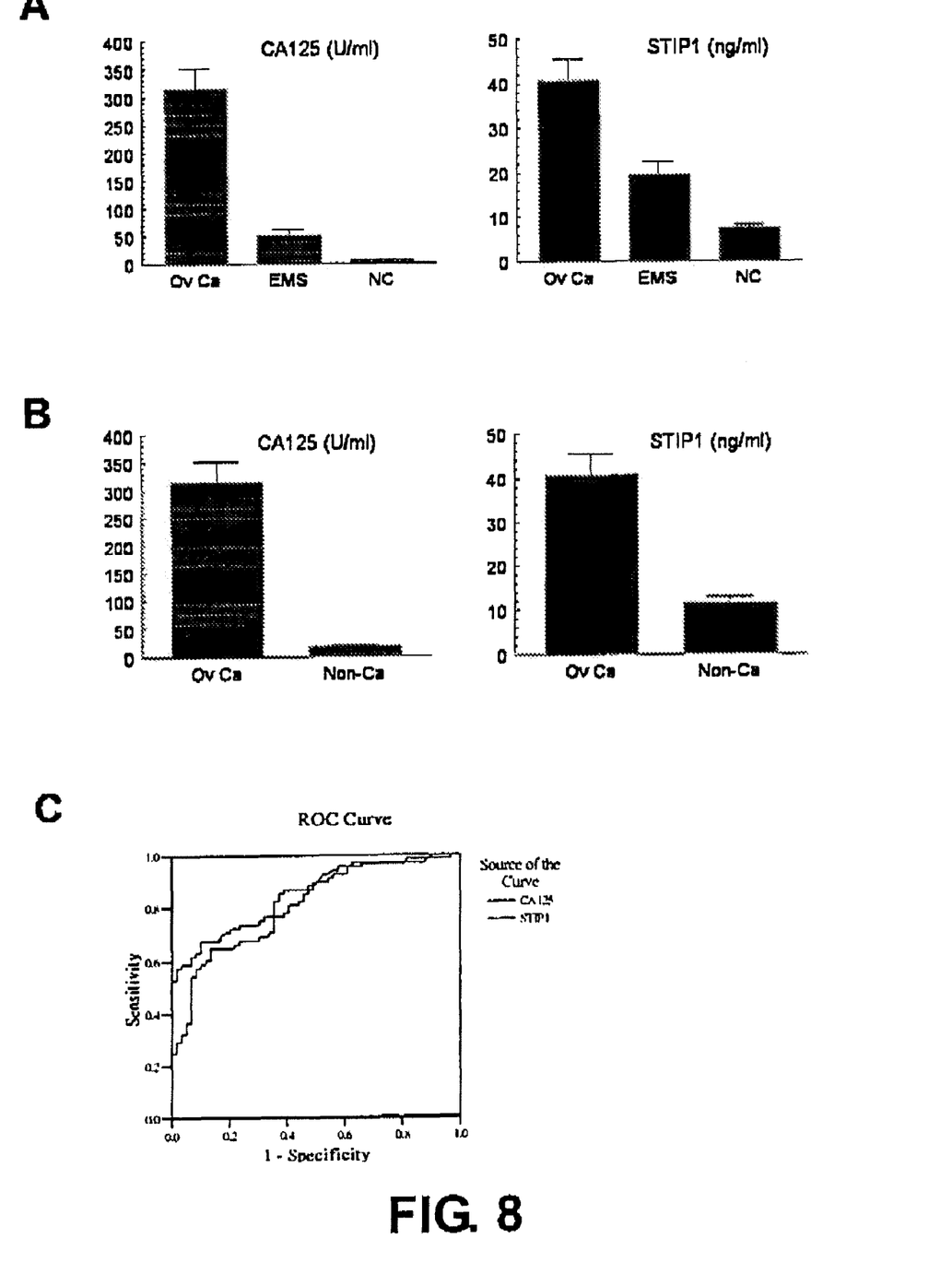

Referring to FIG. 8, panel A, the serum levels of STIP1 were 40.8±4.7 ng/ml (mean±S.E., n=68) in the ovarian cancer group and 19.7±2.9 ng/ml (n=20) in the endometriosis group, both levels being significantly higher than that in the normal control group (7.3±0.9 ng/ml, n=39)($P<0.0001$). Referring to FIG. 8, panel B, the serum level of STIP1 (11.5±1.4 ng/ml) in the non-cancer group (a combination of the normal control group and the endometriosis group, n=59) is also significantly lower than that of the ovarian cancer group ($P<0.0001$).

Referring to FIG. 8, panel A, the serum levels of CA125 are 315.7±36.7 U/ml in the ovarian cancer group (n=667) and 52.1±8.4 U/ml in endometriosis group (n=43), both levels being significantly higher than that in the normal control group (7.9±10.4 U/ml, n=150)($P<0.001$). Referring to FIG. 8, panel B, the serum level of CA125 in the non-cancer group (17.7±2.3 U/ml, n=193) is also significantly lower than that in the ovarian cancer group ($P<0.001$).

Referring to FIG. 8, panel C, the Receiver operating characteristics (ROC) curve analysis of the ovarian cancer group versus the non-cancer group indicate that the area under curve (AUC) were 0.813 for STIP1 and 0.844 for CA125.

Discussion

In the study of this invention, based on the results of image analysis and statistical analysis upon the 2D gels of two groups (4 TIFs and 4 NIFs), the applicants identified protein spots that showed statistical significance. After protein identification, the applicants verified the significant difference of these proteins in these two groups with more samples (9 TIFs and 16 NIFs) using additional protein assays such as Western blot analysis and ELISA. Compared with another experimental approach where researchers did many 2D gels immediately followed by protein identification (Xin Yi et al. (2008), Molecular & Cellular Proteomics, 7: 315-325), the applicants' strategy (FIG. 1) proved to be useful in minimizing the demand of doing 2D gels and protein identification with MALDI-TOF mass spectrometry. The limiting factor of the applicants' approach appears to be the availability of reliable antibodies to validate the identified proteins.

Stress-induced phosphoprotein-1 (STIP1), also known as HSP70/HSP90 organizing protein (HOP), is a 62.6 kDa protein (GeneID 10963; HPRD 05454)(O. O. Odunuga et al. (2004), Bioessays, 26(10):1058-68). STIP1 protein contains 9 tetratricopeptide repeats (TPR) motifs, which are clustered into three domains each consisting of three TPRs, and a nuclear localization signal (NLS) located from amino acid residues 223 to 238 (Human Protein Reference Database). STIP1 has been thought to act primarily as an adapter that directs heat shock protein 90 (HSP 90) to HSP 70-client protein complexes in the cytoplasm, but recent evidence suggests that STIP1 can also modulate the chaperone activities of these HSPs (O. O. Odunuga et al. (2004), supra). TPR motif is a degenerate 34-amino acid sequence, which forms scaffolds that mediate formation of different protein complexes. TPR-containing proteins are found to participate in RNA splicing, transcription, protein folding, signal transduction, and cell cycle regulation (O. O. Odunuga et al. (2004), supra). For instance, nuclear accumulation of STIP1 was noted when the cell cycle was arrested at the G1-S transition (Victoria M. Longshaw et al. (2004), J. Cell Sci., 117(5):701-710), suggesting that the cell cycle status may regulate the nuclear-cytoplasmic shuttling of STIP1.

To the applicants' knowledge, the results of the study of this invention represent a first evidence that STIP1 is secreted by ovarian cancer tissues into peripheral blood of cancer patients. STIP1 has recently been reported to be associated with two other tumors: hepatocellular carcinoma (HCC) (Wei Sun et al. (2007), Molecular & Cellular Proteomics, 6:1798-1808) and glioma (Rafael B. Erlich et al. (2007), GLIA, 55:1690-1698).

Using two-dimensional fluorescence DIGE, He's group identified upregulation of STIP1, three HSP 70 members, and two HSP 90 members in HCC when compared with adjacent non-tumor tissues, suggesting involvement of members of HSP 70 and 90 families in hepatitis B virus-related carcinogenesis (Wei Sun et al. (2007), supra). Martins' group demonstrated that a glioblastoma cell line secreted STIP1 into culture medium, and that treatment with recombinant STIP1 induced proliferation of glioma cells through activation of ERK and PI3K pathways (Rafael B. Erlich et al. (2007), supra).

The applicants' results that recombinant STIP1 significantly induced ERK phosphorylation in ovarian cancer cells (FIG. 7) also supported a functional role of STIP1, which was shown in glioma (Rafael B. Erlich et al. (2007), supra). In the study of this invention, a significant increase of serum levels of STIP1 in ovarian cancer patients than those in normal controls (FIG. 8) clearly indicates that the upregulation of STIP1 in ovarian cancer tissues can be assayed in peripheral blood using a rapid, non-expensive ELISA, such as the one developed herein.

Area under the curve (AUC) in receiver operating characteristics (ROC) curve analyses are frequently used as an evaluation of the usefulness among different diagnostic methods (Mark H. Zweig (1993), supra). Interpretations of ROC results include: outstanding (AUC>0.9), excellent (AUC=0.8~0.9), acceptable (AUC=0.7~0.8), poor (AUC=0.6~0.7), and no discrimination (AUC=0.5). The STIP1 ELISA results obtained herein suggest a comparable value of STIP1 as that of CA125, as shown in AUC of 0.813 for STIP1 and 0.844 for CA125 (FIG. 8, panel C).

Surprisingly, the serum levels of STIP1 in patients with endometriosis were also significantly higher than those in normal controls (FIG. 8, panels A), very much like the higher levels of CA125 that are suggestive for endometriosis. The CA125 ovarian cancer antigen was proved to be a membrane-associated mucin, the gene product of MUC16 (GeneID 94025) (Beatrice W. T. Yin et al. (2001), *J. Biol. Chem.*, 276(29):27371-27375; Beatrice W. T. Yin et al. (2002), *Int. J. Cancer*, 98, 737-740). The heavily O-glycosylated transmembrane MUC16 is a multifunctional molecule linked to the actin cytoskeleton. Upon the identification of mesothelin as a CA125-binding protein, it was proposed that CA125 might contribute to the metastasis of ovarian cancer to the peritoneum by initiating cell attachment to the mesothelial epithelium via binding to mesothelin (Armin Rump et al. (2004), *J. Biol. Chem.*, 279(10):9190-9198; Jennifer A A Gubbels et al. (2006), *Molecular Cancer*, 5 (1):50).

On the other hand, STIP1 appeared to be regulated by cell cycle kinases (Victoria M. Longshaw et al. (2004), supra) and granzyme B (Andrew J. Bredemeyer et al (2006), *J. Biol. Chem.*, 281(48):37130-37141). Given that STIP1 and CA125 function in distinct biological processes, increased levels of STIP1 and CA125 may be used together as complementary biomarkers for ovarian cancer and for endometriosis. To fully validate the use of STIP1, alone or in combination with CA125, as biomarker for these diseases, it is suggested prospective randomized studies with larger sample sizes be conducted.

All patents and literature references cited in the present specification as well as the references described therein, are hereby incorporated by reference in their entirety. In case of conflict, the present description, including definitions, will prevail.

While this invention has been described in connection with specific embodiments thereof, it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

We claim:

1. A method for the detection or preliminary screening of a gynecological disease in a human subject, the gynecological disease selected from the group consisting of ovarian cancers and endometriosis, the method comprising:
obtaining a biological sample from the human subject;
detecting the level of STIP1 in said biological sample; and
comparing the detected level of STIP1 of said biological sample with that of a standard, wherein it is determined that the human subject has the gynecological disease if the detected level of STIP1 of said biological sample is higher than that of the standard.

2. A method for monitoring a gynecological disease in a human subject, the gynecological disease selected from the group consisting of ovarian cancers and endometriosis, the method comprising:
periodically obtaining a biological sample from the human subject;
detecting the level of STIP1 in said biological sample, and
comparing the detected level of STIP1 of said biological sample with that of a standard, wherein it is determined that the human subject has the gynecological disease if the detected level of STIP1 of said biological sample is higher than that of the standard.

3. The method according to claim 1 or 2, wherein the gynecological disease is an ovarian cancer selected from the group consisting of serous papillary carcinoma, serous papillary cystadenocarcinoma, adenocarcinoma, moderately differentiated adenocarcinoma, poorly differentiated adenocarcinoma, endometrioid carcinoma, and combinations thereof.

4. The method according to claim 3, wherein the biological sample is selected from the group consisting of blood, serum, plasma, ovarian tissue, interstitial fluid prepared from ovarian tissue, and combinations thereof.

5. The method according to claim 1 or 2, wherein the gynecological disease is endometriosis selected from the group consisting of endometriosis interna and endometriosis externa.

6. The method according to claim 5, wherein the biological sample is selected from the group consisting of blood, serum, plasma, endometriotic tissue, and combinations thereof.

7. The method according to claim 1 or 2, wherein the level of STIP1 is detected by quantifying STIP1 protein using at least one of the following methodologies selected from the group consisting of gel electrophoresis, Western blotting, enzyme linked immunosorbent assay, radioimmunoassay, immunohistochemistry, and proteomics.

8. The method according to claim 1 or 2, wherein quantifying STIP1 protein is conducted using an antibody-based binding moiety which specifically binds STIP1 protein.

9. The method according to claim 8, wherein the antibody-based binding moiety is labeled with a detectable label.

10. The method according to claim 9, wherein the label is selected from the group consisting of a radioactive label, a hapten label, a fluorescent label, and an enzymatic label.

11. The method according to claim 8, wherein the antibody-based binding moiety is an antibody.

12. The method according to claim 1 or 2, wherein the biological sample is ovarian tissue, and detecting the level of STIP1 is conducted by performing immunohistochemistry assay with the ovarian tissue.

13. The method according to claim 1 or 2, wherein the biological sample is serum, and the level of STIP1 in said sample is detected by an assay selected from the group consisting of Western blotting, enzyme linked immunosorbent assay, radioimmunoassay, immunoradiometric assay, and combinations thereof.

14. The method according to claim 1 or 2, wherein the biological sample is interstitial fluid prepared from ovarian tissue, and the level of STIP1 in said sample is detected by an assay selected from the group consisting of Western blotting, enzyme linked immunosorbent assay, radioimmunoassay, Immunoradiometric assay, and combination thereof.

15. The method according to claim 1 or 2, wherein the method further comprises the steps of
simultaneously detecting the level of CA125 in said biological sample, and comparing the detected level of CA125 of said biological sample with that of a standard.

* * * * *